United States Patent [19]

Moll et al.

[11] Patent Number: 5,520,609
[45] Date of Patent: May 28, 1996

[54] APPARATUS AND METHOD FOR PERITONEAL RETRACTION

[75] Inventors: Frederic H. Moll, San Francisco; Albert K. Chin, Palo Alto; Diane E. Caramore; Frank T. Watkins, III, both of Menlo Park, all of Calif.

[73] Assignee: Origin Medsystems, Inc., Menlo Park, Calif.

[21] Appl. No.: 62,707

[22] Filed: May 18, 1993

Related U.S. Application Data

[63] Continuation of Ser. No. 706,781, May 29, 1991, abandoned.

[51] Int. Cl.$^6$ .................................................. A61B 17/02
[52] U.S. Cl. ........................ 600/204; 600/207; 606/192
[58] Field of Search ........................... 606/192; 604/101; 600/204, 207

[56] References Cited

U.S. PATENT DOCUMENTS

| | | | |
|---|---|---|---|
| 1,060,350 | 4/1913 | Miller . | |
| 1,275,520 | 8/1918 | Bell . | |
| 1,618,261 | 2/1927 | Arbogast . | |
| 1,947,649 | 2/1934 | Kadavy | 128/20 |
| 2,663,020 | 12/1953 | Cushman | 128/303 |

(List continued on next page.)

FOREIGN PATENT DOCUMENTS

| | | | |
|---|---|---|---|
| 516114 | 5/1981 | Australia | A61B 10/00 |
| 0010650 | 5/1980 | European Pat. Off. | A61M 31/00 |
| 0246086 | 11/1987 | European Pat. Off. | A61B 17/02 |
| 0251976 | 1/1988 | European Pat. Off. | A61M 29/02 |
| 0275230 | 7/1988 | European Pat. Off. | A61M 25/00 |
| 2474304 | 7/1981 | France | A61B 17/00 |
| 2646088 | 10/1990 | France | A61M 29/04 |
| 1516411 | 7/1969 | Germany . | |
| 2847633 | 5/1979 | Germany | A61B 17/22E2 |

(List continued on next page.)

OTHER PUBLICATIONS ed. G. Berci, Endoscopy, Appleton–Century–Crofts, 1976, pp. 382–385 and 412.

Unknown—Laparoscopy for Sterilization, Section 1, A Chronology of Laparoscopy.

"New Surgical Procedures for Indirect Hernias" —Product leaflet for Herniastat™ disposable automatic surgical stapling device published by Innovative Surgical Devices, Inc., date unknown.

"A Tiny TV Camera is Fast Transforming Gallbladder Surgery," Wall Street Journal, Dec. 10, 1990, p. A1, Continued on p. A5.

A Comprehensive Guide To Purchasing [Hospital Supplies], V. Mueller & Co, Chicago, 1956, p. 829.

(List continued on next page.)

Primary Examiner—Michael H. Thaler
Attorney, Agent, or Firm—Limbach & Limbach

[57] ABSTRACT

A method and apparatus for mechanically lifting the abdominal wall away from underlying abdominal organs for laparoscopic surgery without insufflation. In the method an expansible device is inserted in the abdominal cavity through a small incision in a collapsed state and then expanded into engagement with an extensive area of the abdominal wall. Lifting force is then applied to the device for peritoneal retraction. The device takes the form of mechanical rods or arms and/or balloons. In the balloon embodiments lifting force may be applied externally of the abdominal cavity, or internally of the cavity by balloon inflation. Certain of the balloon embodiments are of an annular or U-shaped configuration and include a membrane for draping the internal organs and/or a centrally located balloon for lateral expansion. The balloons may be provided with an internal endoscope for viewing. The method also provides for laparoscopic gallbladder removal, either to the interior or exterior of the balloons. A needle is provided to laparoscopically pierce and drain the gallbladder. The needle carries a balloon inflatable to grip the gallbladder for retraction and removal.

7 Claims, 10 Drawing Sheets

U.S. PATENT DOCUMENTS

| | | | |
|---|---|---|---|
| 2,841,148 | 7/1958 | Kadovy | 128/303 |
| 3,039,468 | 6/1962 | Price | 128/347 |
| 3,460,539 | 8/1969 | Anhalt, Sr. | 128/303.17 |
| 3,626,949 | 12/1971 | Shute | 128/344 |
| 3,717,151 | 2/1973 | Collett | 128/347 |
| 3,774,596 | 11/1973 | Cook | 128/5 |
| 3,782,370 | 1/1974 | McDonald | 120/20 |
| 3,831,587 | 8/1974 | Boyd | 128/6 |
| 3,863,639 | 2/1975 | Kleaveland | 128/20 X |
| 3,961,632 | 6/1976 | Moossun | 128/347 |
| 4,052,980 | 10/1977 | Grams et al. | 128/10 |
| 4,077,412 | 3/1978 | Moossun | 128/347 |
| 4,083,369 | 4/1978 | Sinnreich | 128/276 |
| 4,183,102 | 1/1980 | Guiset | 604/101 X |
| 4,240,433 | 12/1980 | Bordow | 138/347 |
| 4,254,762 | 3/1981 | Yoon | 128/4 |
| 4,291,687 | 9/1981 | Sinnreich | 128/129 |
| 4,357,940 | 11/1982 | Muller | 128/303 R |
| 4,430,076 | 2/1984 | Harris | 605/96 |
| 4,447,227 | 5/1984 | Kotsanis | 604/101 X |
| 4,459,978 | 7/1984 | Kotsanis | 128/20 |
| 4,535,773 | 8/1985 | Yoon | 604/51 |
| 4,598,699 | 7/1986 | Garren et al. | 128/4 |
| 4,601,710 | 7/1986 | Moll | 604/165 |
| 4,654,030 | 3/1987 | Moll et al. | 604/165 |
| 4,705,040 | 11/1987 | Mueller et al. | 128/334 R |
| 4,709,697 | 12/1987 | Muller | 128/303 R |
| 4,744,363 | 5/1988 | Hasson | 128/331 |
| 4,763,653 | 8/1988 | Rockey | 604/101 X |
| 4,765,331 | 8/1988 | Petruzzi et al. | 128/303.14 |
| 4,775,371 | 10/1988 | Mueller, Jr. | 604/280 |
| 4,779,611 | 10/1988 | Grooters et al. | 128/4 |
| 4,919,152 | 4/1990 | Ger | 128/898 |
| 4,944,443 | 7/1990 | Oddsen et al. | 227/19 |
| 4,966,583 | 10/1990 | Debbas | 604/98 |
| 4,984,564 | 1/1991 | Yuen | 128/20 |
| 5,002,557 | 3/1991 | Hasson | 606/191 |
| 5,007,898 | 4/1991 | Rosenbluth et al. | 604/54 |
| 5,062,847 | 11/1991 | Barnes | 606/194 |
| 5,082,005 | 1/1992 | Kaldany | 128/850 |
| 5,083,576 | 1/1992 | Ruiz-Razura et al. | 128/898 |
| 5,100,426 | 3/1992 | Nixon | 606/170 |
| 5,122,122 | 6/1992 | Allgood | 604/174 X |
| 5,176,128 | 1/1993 | Andrese | 128/20 |
| 5,176,697 | 1/1993 | Hasson et al. | 606/191 |
| 5,183,464 | 2/1993 | Dubrul et al. | 604/164 X |
| 5,195,505 | 3/1993 | Josefsen | 128/20 |

FOREIGN PATENT DOCUMENTS

| | | | |
|---|---|---|---|
| 8516286 | 9/1985 | Germany | A61B 17/02 |
| 736949 | 5/1980 | U.S.S.R. | A61B 1/00 |
| 797668 | 1/1981 | U.S.S.R. | A61B 17/02 |
| 1367947 | 1/1988 | U.S.S.R. | A61B 17/02 |
| 1577769 | 7/1990 | U.S.S.R. | A61B 17/02 |
| 2071502 | 9/1981 | United Kingdom | A61B 17/02 |
| WO-A9102493 | 3/1991 | WIPO | A61B 17/22 |
| WO-A91/14392 | 10/1991 | WIPO | A61B 1/32 |

OTHER PUBLICATIONS

H. Nagai et al., "A New Method of Laparoscopic Cholecystectomy: An Abdominal Wall Lifting Technique without Pneumoperitoneum," Surgical Laparoscopy and Endoscopy, vol. 1, No. 2, 1991, p. 126.

M. M. Gazayerli, "The Gazayerli Endoscopic Retractor Model 1," Surgical Laparoscopy and Endoscopy, vol. 1, No. 2, 1991, pp. 98–100.

Geza J. Jako & Stephen Rozsos, "Preliminary Report: Endoscopic Laser Microsurgical Removal of Human Gallbladder," J. Laparoendoscopic Surgery, vol. 1, No. 4, 1991.

G. Keen MS, FRCS, (ed.) "Operative Surgery & Management," pp. 334–335, (2nd. ed., Wright, Bristol, 1987).

R. F. Rintoul (ed.), "Farquharson's Textbook of Operative Surgery," pp. 286–289, (7th ed., Churchill Livingston, New York, 1986).

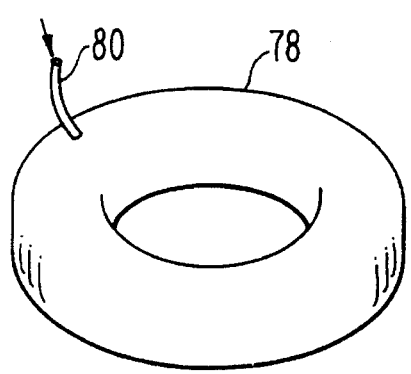
FIG. 24
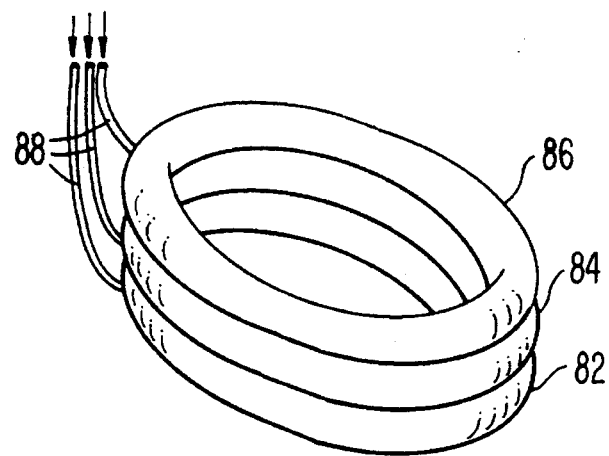
FIG. 25
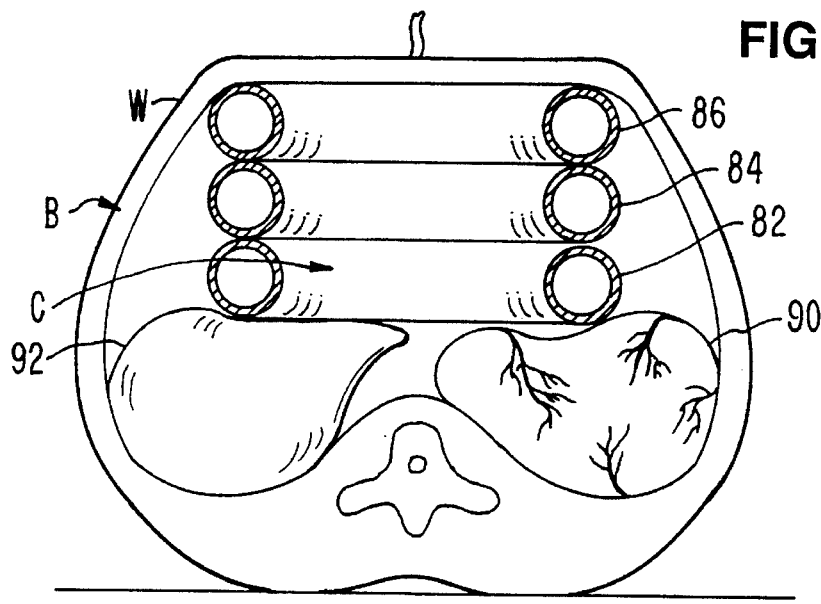
FIG. 26
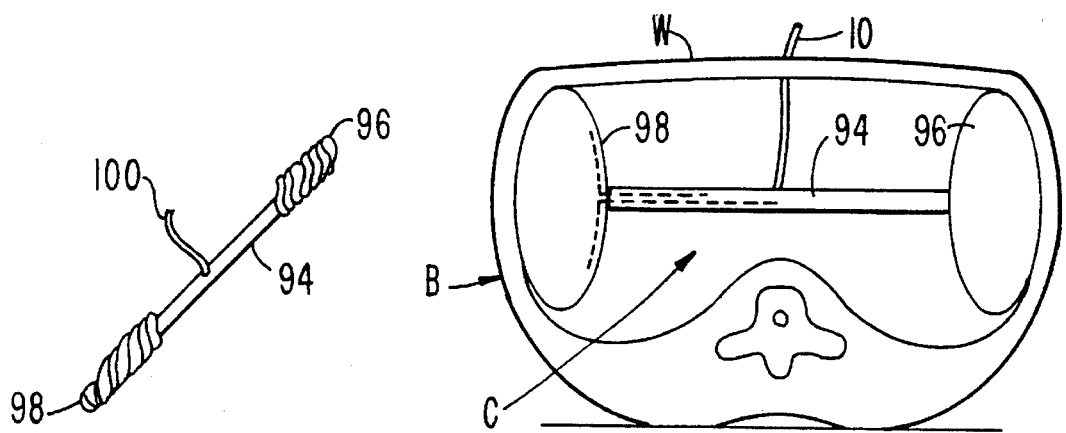
FIG. 27
FIG. 28

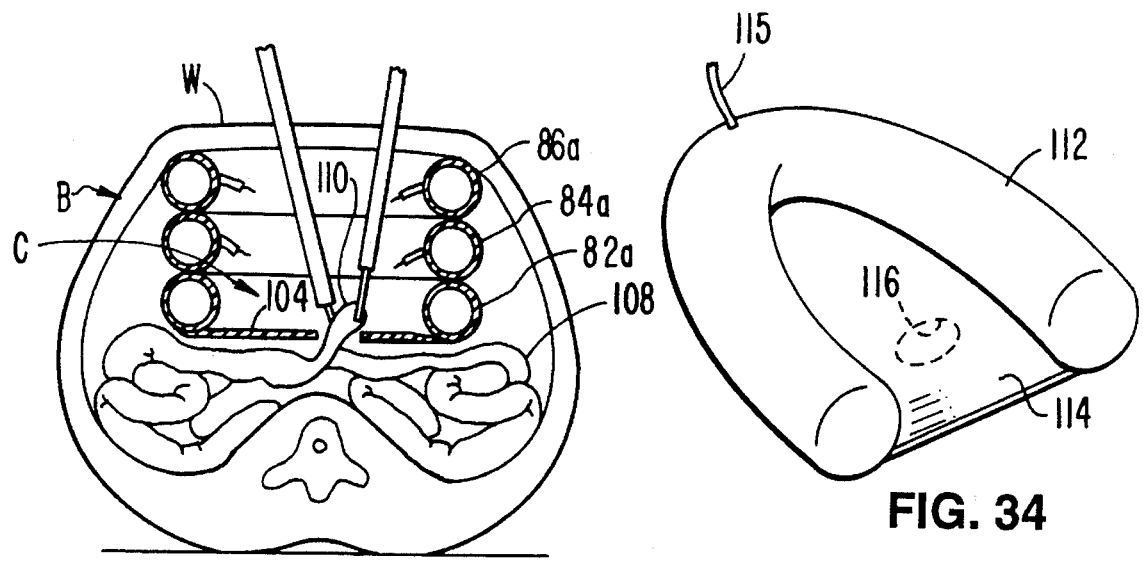
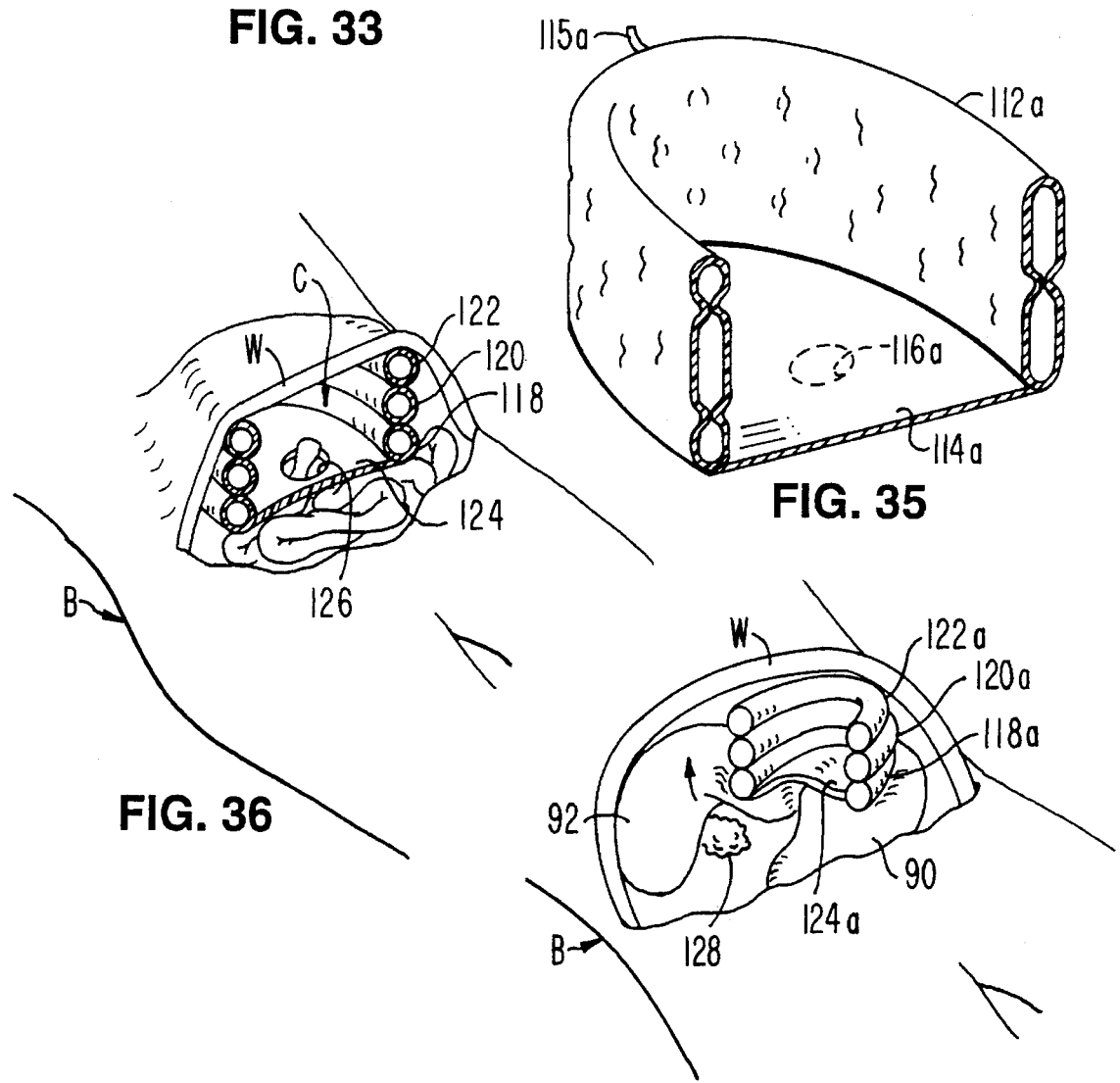
FIG. 33
FIG. 34
FIG. 35
FIG. 36
FIG. 37

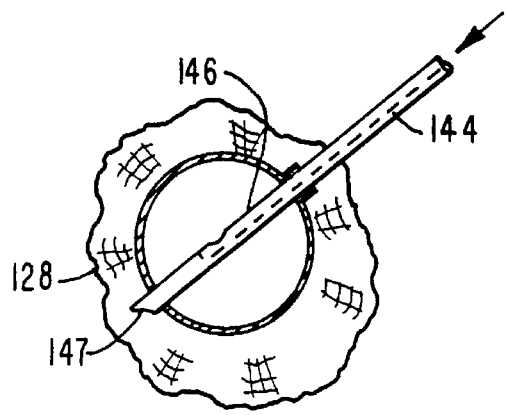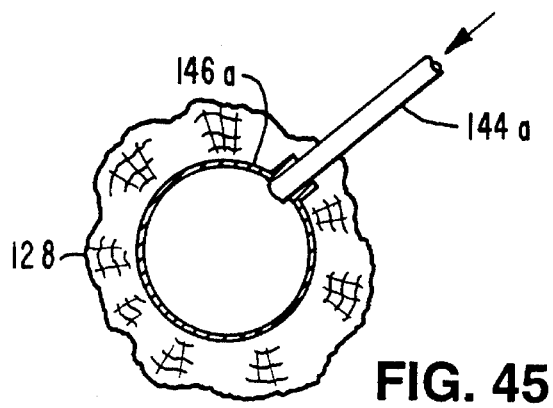
FIG. 44  FIG. 45
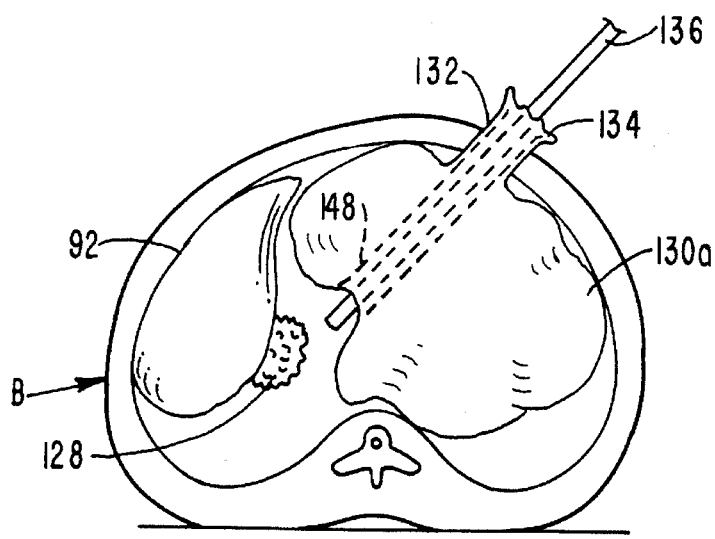
FIG. 46

5,520,609

APPARATUS AND METHOD FOR PERITONEAL RETRACTION

This is a continuation of application Ser. No. 07/706,781 filed on May 29, 1991, now abandoned.

BACKGROUND OF THE INVENTION

The present invention relates to an apparatus and method for mechanically lifting the abdominal wall away from the underlying abdominal organs during laparoscopic procedures. In its more specific aspects, the invention is concerned with such an apparatus and method wherein the abdominal wall is lifted internally by a mechanical device which is introduced blindly or laparoscopically and, once in place, expanded to engage an extensive area of the abdominal wall. The invention is also concerned with an apparatus and method for draping the abdominal organs and displacing a particular organ, such as the gallbladder, for treatment.

Laparoscopy dates back to the turn of the 20th Century. Early laparoscopic techniques were used primarily for diagnostic purposes to view the internal organs, without the necessity of conventional surgery. Since the 1930s, laparoscopy has been used for sterilization and, more recently, for the suturing of hernias. U.S. Pat. Nos. 4,919,152 and 4,944,443 are concerned with techniques of the latter type. Another very recent innovation is the use of laparoscopic surgery for removal of the gallbladder.

The concept of using mechanical retraction schemes to lift the abdominal wall away from the underlying abdominal organs during laparoscopic procedures is new to the present invention. Procedures presently in use use carbon dioxide insufflation to tent up the interior of the abdominal wall. This requires gas seals to be present at all entry ports through the abdominal wall; and because of the doming effect of insufflation, the laparoscopic instruments (graspers, scissors, electrocautery instruments, etc.), need long shafts (on the order of 12 to 13 inches) to reach the treatment site. Such instruments are difficult to control and result in exaggerated movements during instrument application.

SUMMARY OF THE INVENTION

The various mechanical retraction schemes of the present invention allow intraperitoneal placement via small limited incisions or puncture sites. The abdomen does not need to be sealed against gas leaks and doming up of the abdominal wall is avoided. The abdominal wall is lifted by means of either externally disposed posts or mechanical arms, or by means of inflatable bags or balloons which are expanded within the abdomen.

In practice of the method, a small opening is formed in the abdominal wall and the lifting device is inserted into the abdomen through the opening in a contracted state. Once within the abdomen, the device is extended to engage an extensive area of the abdominal wall and the wall is lifted with the device.

In one embodiment, the lifting device takes the form of a compression balloon which is inflated within the abdominal cavity to displace the liver and gallbladder for access. With this arrangement, the gallbladder may be laparoscopically gripped externally of the balloon and dissected. The balloon is transparent and viewing of the procedure is provided through means of an endoscope disposed within or passed through the balloon.

The inventive apparatus comprises expansible abdominal wall engaging means insertable through a small opening in the abdominal wall in a contracted state and, once in place within the abdomen, expansible to engage an extended area of the abdominal wall. Lifting means cooperates with the engaging means to impart lifting force to the abdominal wall through the engaging means. The invention also provides an apparatus for laparoscopically gripping and removing the gallbladder from the abdominal cavity. This apparatus comprises an elongate tubular shaft with a sharpened distal end for piercing the gallbladder and a balloon carried by the shaft for insertion into the gallbladder and expansion into internal gripping engagement therewith. It may also include an opening in the shaft to enable the contents of the gallbladder to be drawn into the shaft.

A principal object of the present invention is to provide a peritoneal retraction system to lift the abdominal wall without insufflation.

Another and related object of the invention is to provide such a system which avoids the requirement of gas seals to be present at all entry ports through the abdominal wall.

Still another object of the invention is to provide such a system which avoids doming of the abdominal wall and the requirement that the laparoscopic instruments be very long in order to accommodate such doming.

Yet another object related to the latter object is to enable laparoscopic surgery to be carried out with instruments having relatively short shafts and to thus ease and increase the control imparted to the instruments by the surgeon.

A further object of the invention is to provide a peritoneal retraction system which drapes the abdominal organs and may serve to displace a particular organ for treatment.

Another object of the invention is to provide a peritoneal retraction system which is gentle and may be controlled to effect the lifting of discreet areas of the abdominal wall.

Yet another object of the invention is to provide a peritoneal retraction system which employs a balloon within or through which an endoscope may be placed for viewing a laparoscopic operation to the outside of the balloon.

Yet another and more specific object of the invention is to provide a laparoscopic instrument internally engagable with an organ to be treated to distend and manipulate the organ or withdraw the organ from the body.

Still another object related to the latter object is to provide such an instrument which may be used to withdraw the contents of the organ prior to its removal.

Yet another object of the invention is to provide a system of lifting the abdominal wall for peritoneal retraction which avoids unduly tensioning body tissue.

Another general object of the invention is to provide such a system which avoids gas leaks and the need for trocar valves.

These and other objects will become more apparent when viewed in light of the following detailed description and accompanying drawings.

BRIEF DESCRIPTION OF THE DRAWINGS

FIG. 24 is a perspective view of the lifting device of an eighth embodiment of the invention wherein the device takes the form of a single inflatable toroidal balloon;

FIG. 25 is a perspective view of the lifting device of a ninth embodiment of the invention wherein the device takes the form of three superimposed inflatable toroidal balloons;

FIG. 26 is a transverse cross-sectional view of a body showing the lifting device of the ninth embodiment of the invention in the process of lifting the abdominal wall;

FIG. 27 is a perspective view of the lifting device of a tenth embodiment of the invention wherein the device takes the form of a tubular rod having balloons at its distal ends, with the balloons shown in the contracted state;

FIG. 28 is a transverse cross-sectional view of a body, showing the lifting device of tenth embodiment in the process of lifting the abdominal wall;

FIG. 33 is a cross-sectional elevational view similar to FIG. 32, illustrating a pair of laparoscopic instruments extended through the center balloon and draping membrane of the eleventh embodiment lifting device to surgically treat the intestines;

FIG. 34 is a perspective view of the lifting device of the twelfth embodiment of the invention wherein the device takes the form of a single U-shaped balloon having a draping member secured thereacross;

FIG. 35 is a perspective view of a modified version of the lifting device for the twelfth embodiment wherein the device takes the form of a single U-shaped balloon having a draping member secured thereacross, with the walls of the balloon being tacked together at discreet locations;

FIG. 36 is a perspective view of the lifting device of a thirteenth embodiment of the invention shown in place within the abdominal cavity of a body, with parts broken away and shown in section to illustrate the device in treating relationship to the intestines;

FIG. 37 is a perspective view of a lifting device of a fourteenth embodiment of the invention shown in place within the abdominal cavity of a body, with parts broken away and shown in section to illustrate the device displacing the liver for exposure of the gallbladder;

FIG. 44 is a cross-sectional view showing the gallbladder distension and manipulation device of FIGS. 41 to 43 in inflated condition within the gallbladder;

FIG. 45 is a cross-sectional view showing a modified version of the device of FIG. 44 wherein the device has a single lumen for inflation of the balloon and no lumen for withdrawal of the contents of the gallbladder; and FIG. 46 is a transverse cross-sectional view similar to FIG. 38, showing a modified version of the fifteenth embodiment wherein the endoscope extends fully through the balloon of the lifting device.

DETAILED DESCRIPTION OF THE INVENTION

In those embodiments of the present invention which employ balloons, the balloon material should be relatively inelastic and tough. Examples of such material are Mylar, Polyethylene and Polyurethane. The thickness of the balloon wall is typically from 0.5 to 5 mils.

Figure 1:
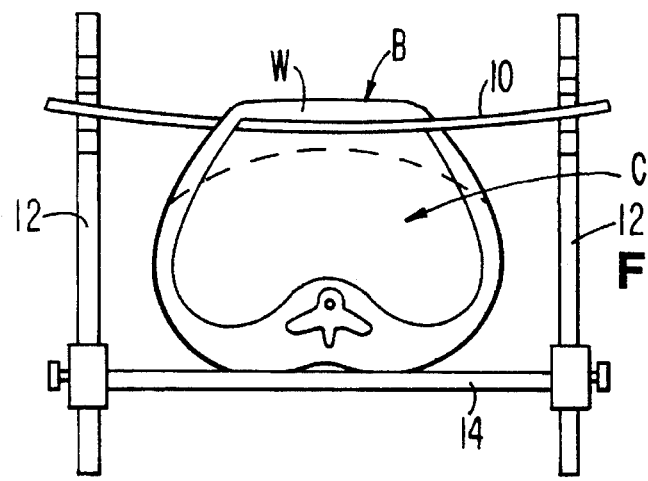
FIG. 1 is a transverse cross-sectional elevational view of a body, showing a first embodiment of the invention in the process of lifting the abdominal wall.

Referring now to FIG. 1, a body is designated therein in its entirety by the letter "B" and is shown having an abdominal cavity "C" with an upper wall "W". The solid lines illustrate the wall in the retracted elevated condition. The phantom lines depict the position the wall would assume when relaxed.

The lifting device of the first embodiment (FIG. 1) comprises a stiff transverse bar 10 passed through a puncture site below the costal margin on one side of the body and out another puncture site below the costal margin on the other side. The puncture sites are placed as far laterally as possible; close to the anterior axiallary line on both sides. The bar is then lifted and placed on slotted posts 12 secured to both sides of the operating table 14. The placement of the bar below the costal margin places the maximum lift at the site of the gallbladder, for cholecystectomy procedures. The bar may be placed through puncture sites located more inferiorly for other procedures. A second transverse bar may also be used to define an entire plane of lift, as four puncture sites are then made in the abdominal wall. Alternatively, instead of using a rigid bar, a cable may be passed through the abdominal wall and variable tension applied to the cable to yield different degrees of retraction.

Figure 2:
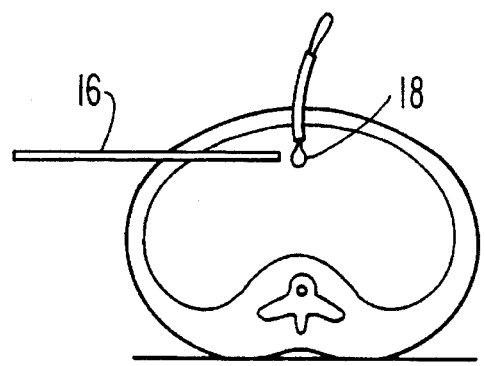
FIG. 2 is a transverse cross-sectional elevational view of a body, showing a second embodiment of the invention in the process of being placed for lifting of the abdominal wall.
Figure 3:
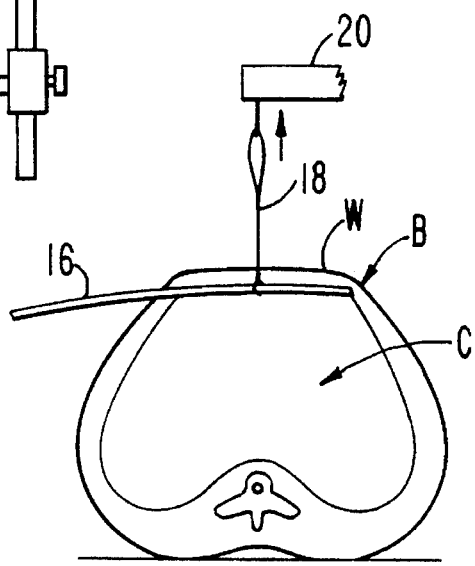
FIG. 3 is a transverse cross-sectional view similar to FIG. 2, showing the second embodiment in the process of lifting the abdominal wall.

In the second embodiment (FIG. 2) a stiff bar 16 is passed into the abdominal cavity through one side. A small puncture is then made at the mid-line of the abdominal wall and the cable loop 18 is then passed into the abdominal cavity. The bar 16 is passed through the loop and the loop is then pulled up (FIG. 3) to achieve retraction. Directional control of the bar is maintained by the portion of the bar that remains outside the abdomen.

Figure 4:
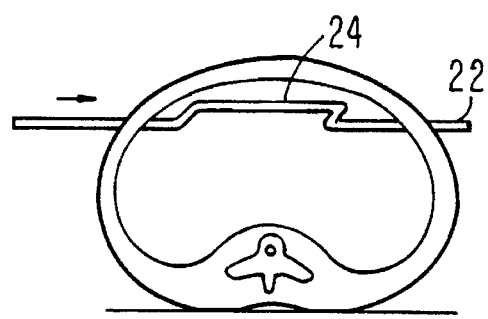
FIG. 4 is a transverse cross-sectional elevational view of a body, showing a third embodiment of the invention in the process of being placed for lifting of the abdominal wall.
Figure 5:
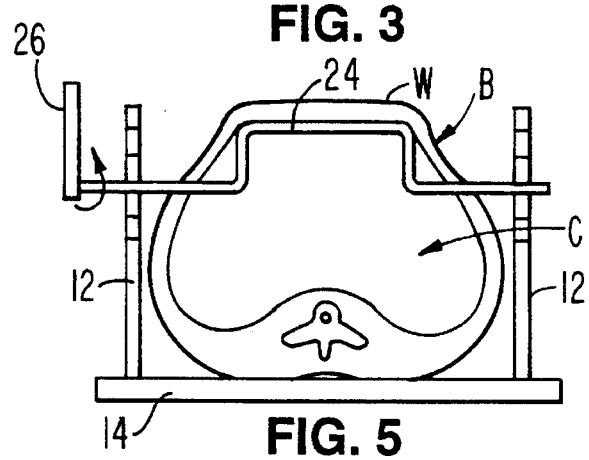
FIG. 5 is a transverse cross-sectional view similar to FIG. 4, showing the third embodiment in the process of lifting the abdominal wall.

The lifting device of the third embodiment (FIGS. 4 and 5) comprises a rigid rod 22 having a lateral offset 24 of a generally rectangular shape. The rod 22 is threaded through entry and exit puncture sites in the abdominal wall and then rotated and clamped down to provide retraction, as shown in FIG. 5. Slotted posts 12 support the proximal and distal ends of the rod. A crank 26 is engaged with one of the ends of the rod to rotate it to the retraction position.

Figure 6:
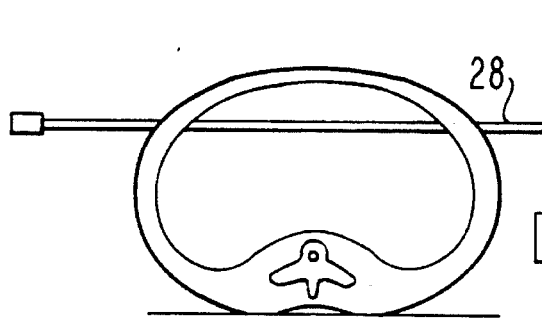
FIG. 6 is a transverse cross-sectional view of a body, showing a fourth embodiment of the invention in the process of being placed for lifting of the abdominal wall.
Figure 7:
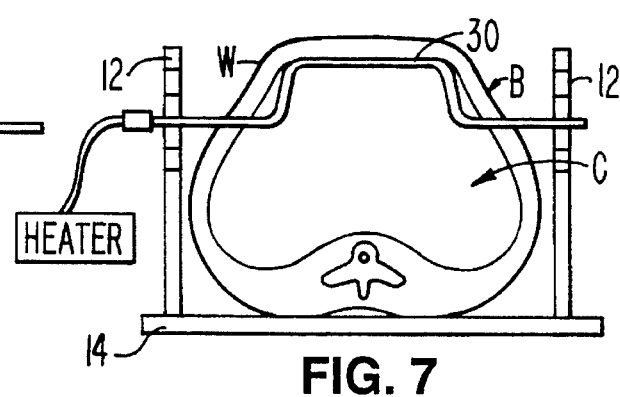
FIG. 7 is a transverse cross-sectional view similar to FIG. 6, showing the fourth embodiment in the process of lifting the abdominal wall.

The fourth embodiment (FIGS. 6 and 7) is essentially a variation of the third embodiment. In the fourth embodiment, the rod 28 is fabricated of a shape-memory metal, such as NITINOL® which is straight when cool and assumes a shape with a laterally offset central portion 30 when heated. An electrode (not illustrated) embedded into the rod is used to heat the rod at the transition site, causing the rod to convert to a rectangular shape for retraction, as seen in FIG. 7.

The rod 28 is passed through the abdomen at puncture sites located at the costal margins, similarly to the FIG. 1 embodiment. Once in place, the proximal and distal ends of the rod are engaged on slotted posts 12. A heater 32 (see FIG. 7) is then activated to increase the rod temperature at the transition site, resulting in retraction of the abdominal wall.

The fifth embodiment shown in FIGS. 8 to 11 comprises a pair of angle-shaped rigid members 34 and 36 having intermediate sections 38 and 40 extending in generally parallel relationship to one another and rotatably received within a sleeve 42. The proximal ends of the members 34 and 36 are formed with operating levers 44 and 46, respectively. The distal ends of the members 34 and 36 are provided with elongate arms 48 and 50.

Figure 8:
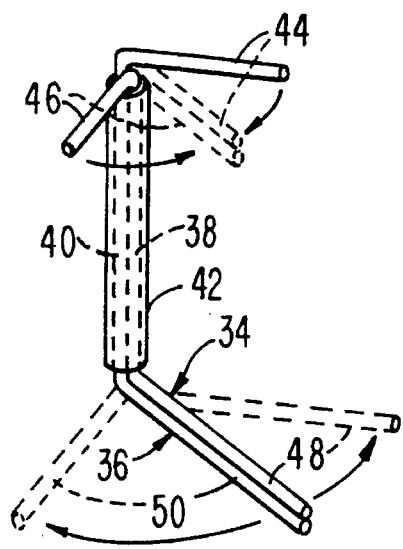
FIG. 8 is a perspective view of the lifting device of a fifth embodiment of the invention, with solid lines showing the device in contracted condition and phantom lines showing the device in the expanded condition.
Figure 9:
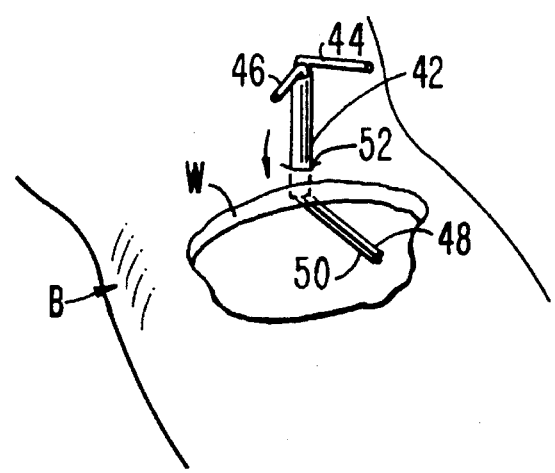
FIG. 9 is a perspective view of a body in the process of having the fifth embodiment lifting device inserted into place in the contracted condition, with the abdominal wall broken away for purposes of illustration.
Figure 10:
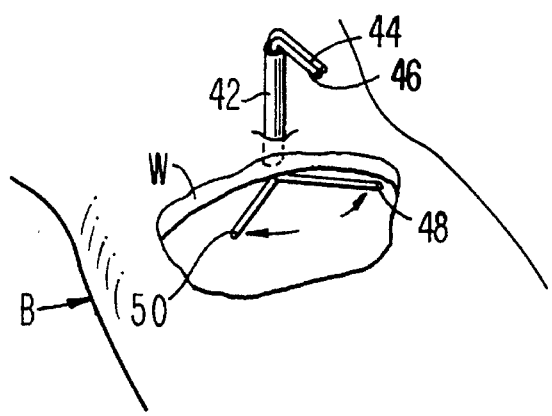
FIG. 10 is a perspective view similar to FIG. 9, showing the lifting device of the fifth embodiment in the process of being expanded.

In use of the fifth embodiment, an incision 52 is cut into the abdominal wall and the arms 48 and 50 are extended through the incision while in the contracted condition shown in FIGS. 8 and 9. The levers 44 and 46 are then moved toward one another and held together to fan the arms outwardly beneath the abdominal wall, as shown in FIG. 10. The abdominal wall may then be lifted as shown in FIG. 11 to retract the abdomen.

Figure 12:
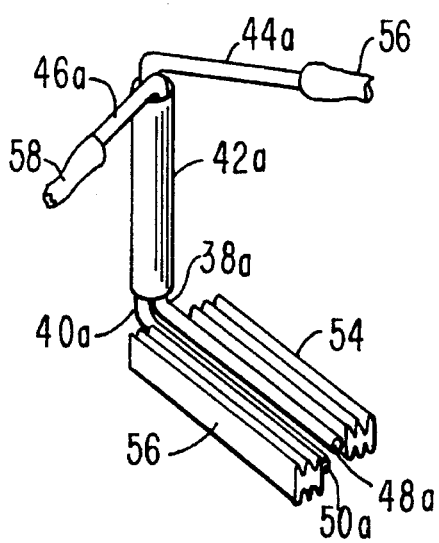
FIG. 12 is a perspective view of the lifting device of a sixth embodiment of the invention, with the device shown in contracted condition and the balloons therein deflated.
Figure 13:
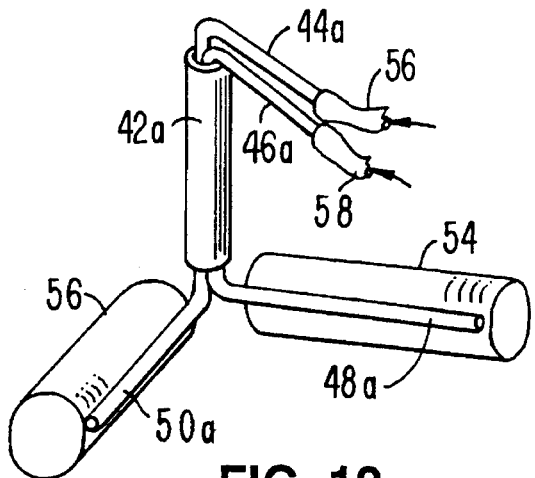
FIG. 13 is a perspective view of the lifting device of the sixth embodiment, with the device shown in expanded condition and the balloons inflated.

The sixth embodiment shown in FIGS. 12 and 13 differs from the fifth embodiment only in that the arms, designated $48_a$ and $50_a$, carry elongate balloons 54 and 56, respectively, and that the angle-shaped members are tubular to provide for the conduit of inflation gas to these balloons. The elements of the FIGS. 12 and 13 embodiments corresponding to those of the embodiments shown in FIGS. 8 to 10 are designated by like numerals, followed by the subscript "a" as follows: intermediate sections $38_a$ and $40_a$; sleeve $42_a$; and arms $44_a$ and $46_a$. Flexible conduits 56 and 58 are secured to the levers $44_a$ and $46_a$ to provide for the conduit of gas thereto to inflate the balloons 54 and 56.

Figure 11:
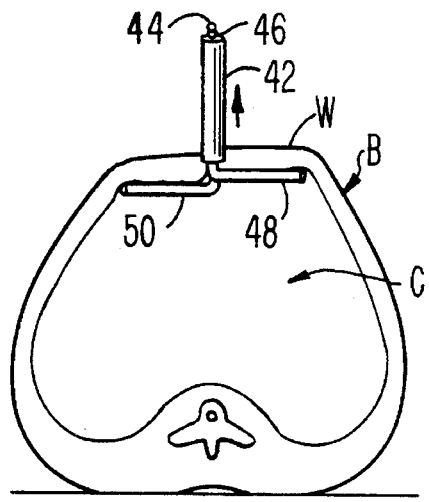
FIG. 11 is a transverse cross-sectional elevational view of a body showing the fifth embodiment of the invention in the process of lifting the abdominal wall.

The sixth embodiment is introduced into the abdominal cavity and used for retraction in generally the same manner depicted in FIG. 9 to 11, with the exception that after the arms $48_a$ and $50_a$ are fanned out, the balloons 54 and 56 would be inflated, as shown in FIG. 13. This expands and cushions the area of contact between the arms and abdominal wall.

Figure 14:
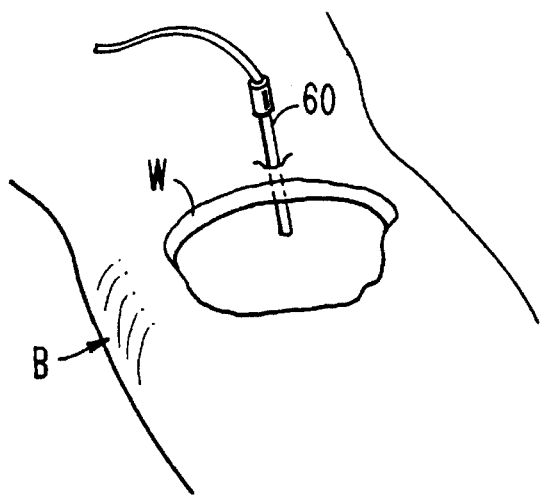
FIGS. 14 to 19 are perspective views sequentially illustrating the steps of inserting the fifth embodiment lifting device into place within the abdominal cavity and expanding the device for engagement with the abdominal wall, with part of the abdominal wall broken away for purposes of illustration.
Figure 15:
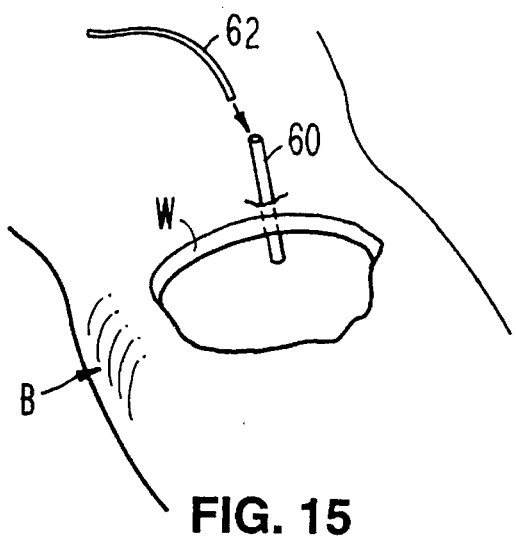
Figure 16:
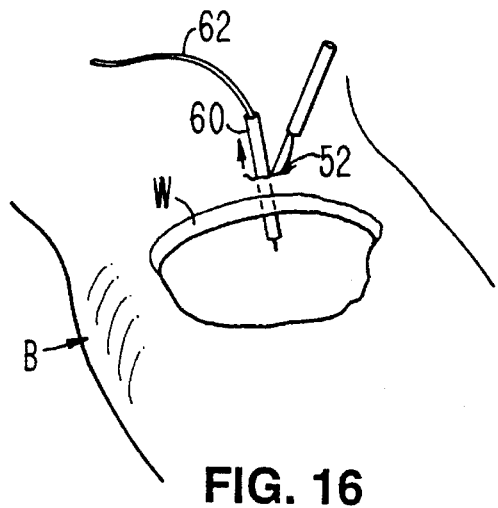
Figure 17:
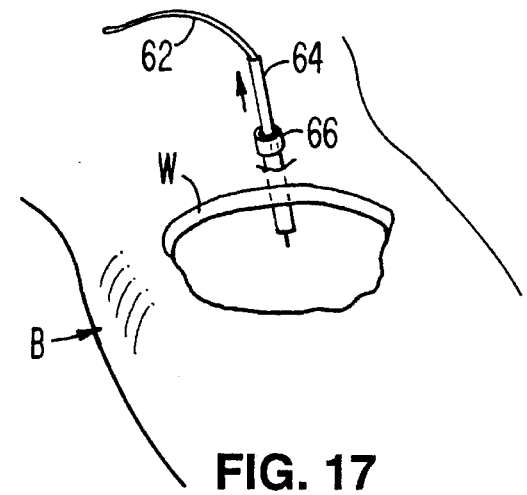
Figure 18:
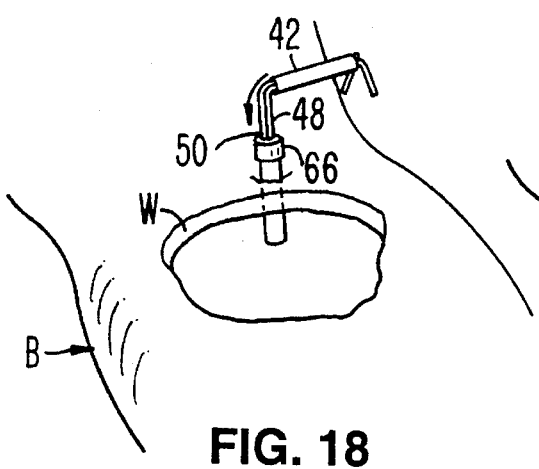
Figure 19:
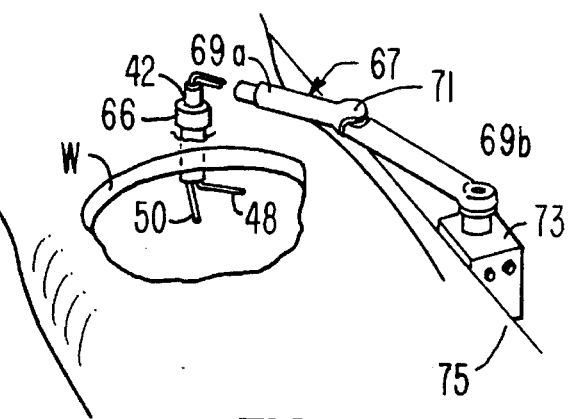

FIGS. 14 to 19 illustrate the preferred sequence for forming the incision 52 and introducing the fifth or sixth embodiment into the abdominal cavity. In FIG. 14, a Veress needle with a thin plastic sheath 60 forms a puncture in the abdominal wall and enters the abdominal cavity. The Veress needle is then withdrawn, leaving the sheath 60 in place as shown in FIG. 15 and the guidewire 62 is threaded through the sheath and into the abdominal cavity. A small incision 52 (0.5 cm) is then made along the sheath adjacent the guidewire and the sheath is removed, leaving the guidewire in place as shown in FIG. 16. A dilator 64 having a plastic guide sheath 66 thereover is then advanced over the guidewire and into the abdomen as shown in FIG. 17 and then the dilator and guidewire are removed, leaving the sheath in place as shown in FIG. 18. The dilator may have a fiberoptic scope to ensure that no bowel loops are impacted by the sheath during its placement. The lifting device or retractor is then introduced into the abdominal cavity through the guide sheath, as shown in FIG. 18, with the sheath protecting abdominal organs from trauma during insertion. Thereafter, the arms 48 and 50 are fanned out to provide expanded engagement with the inside of the abdominal wall, as shown in FIG. 19. There it will also be seen that a mechanical arm 67 is being engaged with the levers 44 and 46 to impart lifting force thereto and, in turn, retract the abdominal wall. The arm 67 has a distal section 69$_a$ and a proximal section 69$_b$ connected by a lockable swivel 71. The proximal section is supported on a motorized worm gear actuator 73 mounted on the side of the operating table, designated 75.

Figure 20:
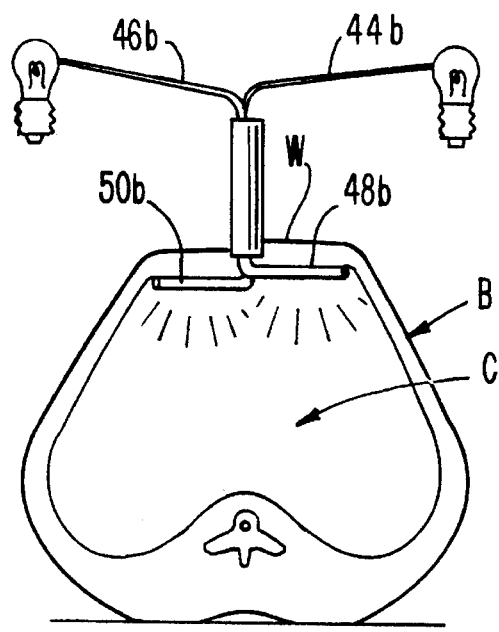
FIG. 20 is a transverse cross-sectional elevational view of a body, showing a modified version of the fifth embodiment lifting device in the process of lifting the abdominal wall, wherein the device is shown illuminating the area beneath the wall.
Figure 22:
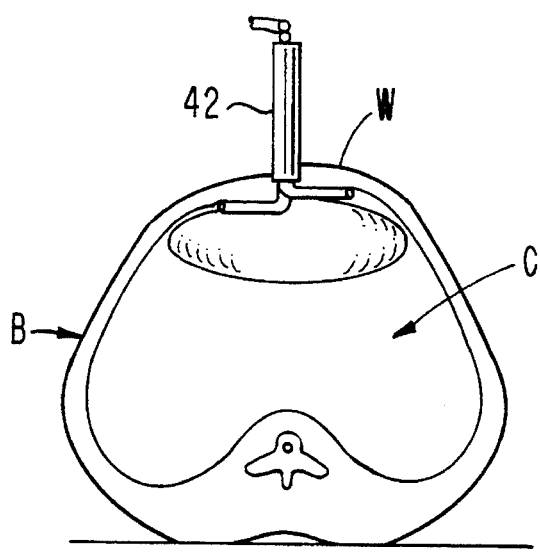
FIG. 22 is a transverse cross-sectional elevational view of a body showing yet another modified version of the fifth embodiment device wherein the expansible legs of the device carry a lifting balloon.

The modified version of the fifth embodiment shown in FIG. 20 corresponds in structure and mode of operation to that of FIGS. 8 to 11, except that lifting arms 48$_b$ and 50$_b$ incorporate fiberoptic means to illuminate the abdominal cavity. FIG. 20 diagrammatically shows light bulbs 68 at the proximal ends of the levers 44$_b$ and 46$_b$ to provide a light source for the fiberoptic illuminators.

Figure 21:
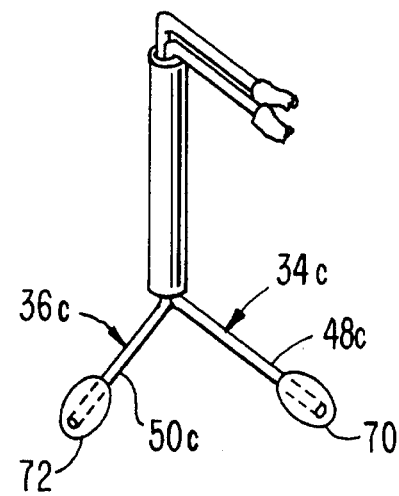
FIG. 21 is a perspective view of another modified version of the fifth embodiment lifting device wherein the distal ends of the expansible elements are provided with balloons to shield them against snagging on body tissue.

The modified fifth embodiment version of FIG. 21 differs from that of FIGS. 8 to 11 only in that the angle-shaped members 34$_c$ and 36c are tubular and provided with inflatable balloons 70 and 72 at the distal ends of the arms 48$_c$ and 50$_c$. These balloons serve to shield the internal body organs from the ends of the arms. In use, the balloons would be in a contracted deflated condition during introduction of the FIG. 21 lifting device into the abdominal cavity. Once in place within the cavity, the balloons would be inflated through the tubular angle members and the arms 34c and 36c would be spread to fan out beneath the abdominal wall.

Figure 23:
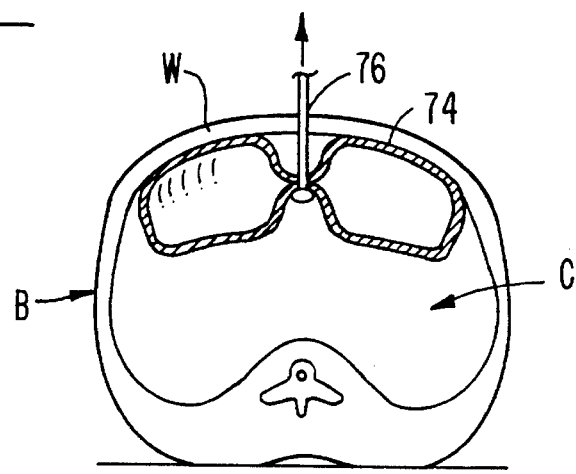
FIG. 23 is a transverse cross-sectional elevational view of a body showing a seventh embodiment of the invention in the process of lifting the abdominal wall.
Figure 29:
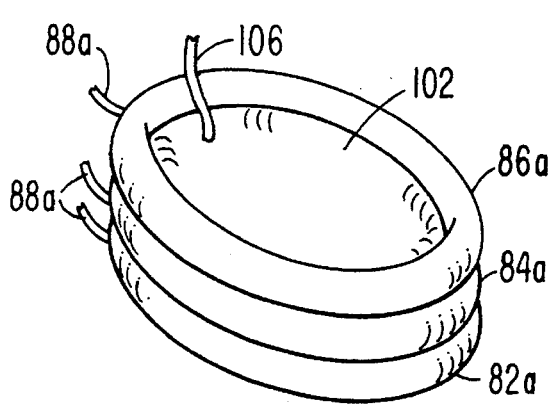
FIG. 29 is a perspective view of the lifting device of an eleventh embodiment of the invention, wherein the device takes the form of three superimposed toroidal balloons with a draping membrane extending across the lowermost balloon and a centrally disposed expansion balloon disposed within the two uppermost toroidal balloons.

The seventh embodiment lifting device of FIG. 23 comprises a balloon 74 secured to the distal end of a tubular lifting rod 76. In use, the rod 76 with the balloon in deflated condition wrapped closely therearound is introduced into the abdominal cavity through a small incision. The balloon is then inflated through the rod to expand into extended contact with the abdominal wall, as shown in FIG. 23. A mechanical arm is then used to raise the rod 76 as depicted by the arrow line in FIG. 23 and, in turn, retract the abdominal wall.

The eighth embodiment lifting device shown in FIG. 24 simply comprises a toroidal balloon 78 having an inflation conduit 80 secured in fluid communication therewith. This balloon is deflated and tightly contracted for introduction into the abdominal cavity through a small incision. Once in place, it is inflated to expand into extended engagement with the abdominal wall and lift the wall, similar to the depiction of the ninth embodiment shown in FIG. 26.

The ninth embodiment illustrated in FIGS. 25 and 26 differs from the eighth embodiment of FIG. 24 primarily in that the lifting device comprises three superimposed toroidal balloons 82, 84 and 86 having inflation conduits 88 secured in fluid communication therewith. In use, the eighth embodiment is deflated and collapsed to a tightly wound condition for introduction into the abdominal cavity through a small incision. Once in place, the balloons 82, 84 and 86 are inflated, as shown in FIG. 26, to retract the abdominal wall. From the latter figure it will be seen that the lowermost toroidal balloon 82 rests on the stomach 90 and the liver 92 and that retraction or lifting force results from expansion of the superimposed balloon elements within the abdominal cavity so as to assume a condition in compression between the abdominal wall and the organs therebeneath. No external lifting device, such as that of the aforedescribed embodiments, is required for the eighth and ninth embodiments.

The lifting device of the tenth embodiment depicted in FIGS. 27 and 28 comprises a tubular rod 94 having balloons 96 and 98 secured in sealed fluid communication with the distal ends thereof. An inflation conduit 100 is secured in sealed fluid communication with the rod to provide inflation gas for the balloons. The balloons are proportioned to assume an ovaloid expanded condition upon inflation, as seen in FIG. 28.

In use, the tenth embodiment lifting device is introduced into the abdominal cavity through a small incision and then maneuvered to dispose the rod 94 in a generally horizontal condition as shown in FIG. 28. The conduit 100 is extended through the incision in the abdominal wall and extends to a suitable source of fluid pressure. Once in place within the abdominal cavity, the balloons 96 and 98 are inflated to spread and lift the abdominal wall as shown in FIG. 28.

The eleventh embodiment depicted in FIGS. 29 to 33 is similar to the ninth embodiment, with the addition that it is provided with a centrally disposed secondary balloon 102 and a draping membrane 104. The superimposed toroidal balloons of the eleventh embodiment and the inflation conduits therefor are designed by numerals corresponding to those of the ninth embodiment, followed by the subscript "a" as follows: 82$_a$; 84$_a$; 86$_a$; and 88$_a$.

Figure 30:
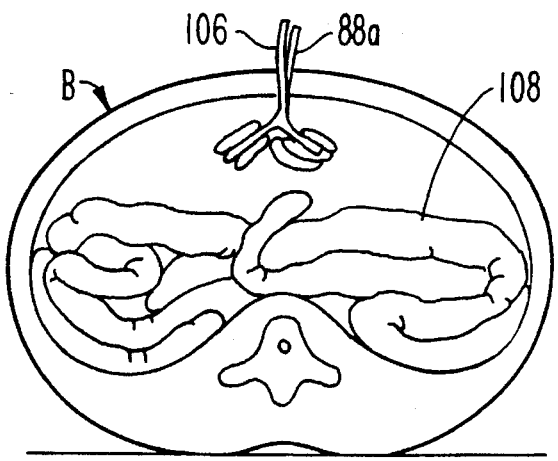
FIGS. 30, 31 and 32 are transverse cross-sectional elevational views of a body, sequentially illustrating the eleventh embodiment lifting device in the process of being inserted into the abdominal cavity above the intestines and inflated to lift the abdominal wall and drape the intestines.
Figure 31:
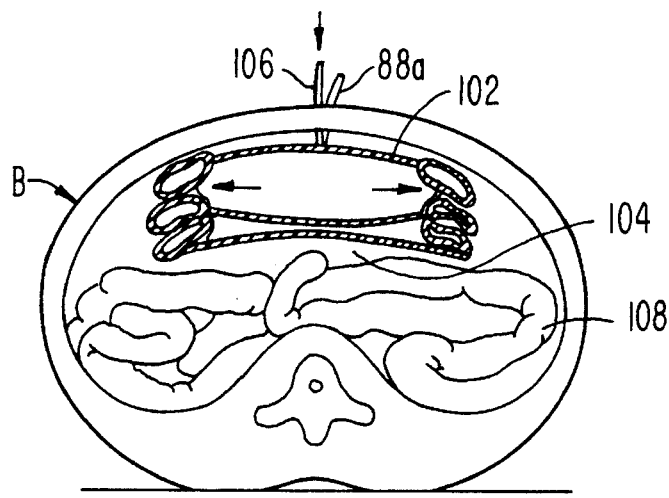
Figure 32:
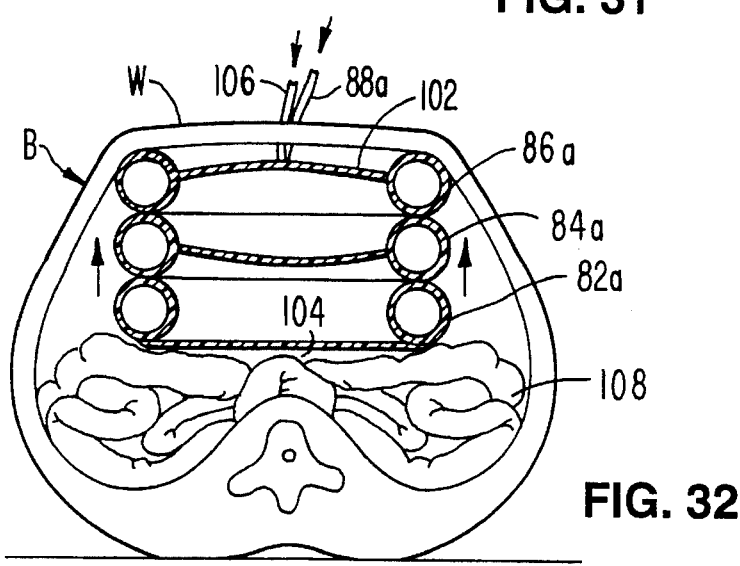

In use, the eleventh embodiment is collapsed as shown in FIG. 30 and introduced into the abdominal cavity through a small incision. Once within the cavity, the balloon 102 is inflated through an inflation conduit 106 therefor which extends through the incision. Inflation of the balloon 102 functions to laterally expand the toroidal balloons as depicted in FIG. 31. Thereafter, the toroidal balloons are inflated through the conduits 88$_a$ to effect lifting and retraction of the abdominal wall, as shown in FIG. 32. There it will be seen that the lowermost toroidal balloon 82$_a$ and the membrane 104 rest on the intestines 108.

FIG. 33 shows how laparoscopic operating tools may be extended through the abdominal wall and the central passage provided by the toroidal balloons 82$_a$, 84$_a$ and 86$_a$. As there illustrated, it will be seen that the balloon 102 has been fractured and that an opening 110 has been formed in the membrane 104. Notwithstanding that the opening 110 interrupts the continuity of the membrane and provides for the access of the intestine therethrough, the part of the membrane which remains intact continues to drape over and shield that area of the intestine which is not to be treated.

The twelfth embodiment lifting device shown in FIG. 34 is essentially a variation of the eleventh embodiment device wherein, rather than employing three superimposed balloons with a secondary lateral expansion balloon, the lifting device comprises a single U-shaped balloon 112 having a draping membrane 114 secured thereacross. In use, the twelfth embodiment balloon would be introduced into the abdominal cavity and inflated in much the same manner as the eleventh embodiment balloon, with the exception that no secondary central expansion balloon would be provided. The balloon 112 would be selectively inflated through means of a conduit 115 which communicates therewith and extends through a small incision in the abdominal wall. The membrane 114 would serve to drape and shield the internal body organs. Phantom lines 116 depict how an opening might be formed through the membrane to provide access to the organs therebeneath, while the membrane continues to drape and shield the organs which are not to be treated.

The lifting device of FIG. 35 corresponds to that of FIG. 34, with the exception that the U-shaped balloon has tacked sidewalls to provide an extended balloon height upon inflation. The parts of the FIG. 35 corresponding to those of the FIG. 34 device are designated by like numerals, followed by the subscript "a" as follows: balloon 112$_a$; membrane 114$_a$; conduit 115$_a$; and phantom line opening 116$_a$.

The thirteenth embodiment device shown in FIG. 36 is essentially the same as the embodiment of FIG. 35, with the exception that the U-shaped balloon is comprised of three superimposed U-shaped balloons, rather than a single balloon with tacked walls. As there shown, the three balloons are designated by the numerals 118, 120 and 122 and a draping membrane 124 is secured across the lowermost balloon 118. It should be appreciated that the lifting device of FIG. 36 would be introduced into the abdominal cavity in deflated condition through a small incision. Once in place, the balloons 118, 120 and 122 would be inflated through means of a conduit extending through the incision in the cavity. Rather than cutting the membrane 124 during the surgery, the membrane is preformed with an opening 126 which provides access to the area of the organ to be treated.

The fourteenth embodiment lifting device shown in FIG. 37 has a configuration similar to that of the FIG. 36 embodiment, with the exception that the balloons are proportioned to rest on the stomach 90 while depressing the liver 92 for displacement and exposure of the gallbladder 128. As shown in FIG. 37, the lifting device comprises superimposed U-shaped balloons $118_a$, $120_a$ and $122_a$, with a draping membrane $124_a$ secured across the lowermost balloon $118_a$. It should be appreciated that the device of FIG. 37 would be introduced into the abdominal cavity through a small incision in a deflated contracted state and, once in place, selectively inflated to lift the abdominal wall.

The fifteen embodiment depicted in FIGS. 38 to 44 employs a transparent balloon 130 which serves as the lifting device. The balloon is contracted and introduced into the abdominal cavity through a small incision 132. The neck of the balloon, designated 134 is maintained in a condition extending through the incision and provides both for the inflation of the balloon and for the extension of an endoscope 136 into the balloon. The neck and the endoscope are so proportioned as to provide a generally fluid tight seal therebetween. As shown, the balloon 130 depresses the liver 92 to expose the gallbladder 128 for treatment and viewing through the endoscope 136.

Figure 39:
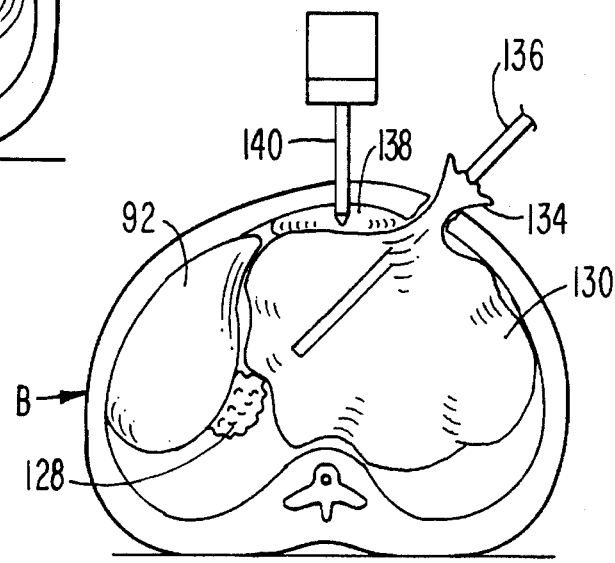
FIG. 39 is a transverse cross-sectional view similar to FIG. 38, illustrating a modified version of the fifteenth embodiment wherein a secondary balloon is positioned above the primary balloon to shield the primary balloon from a trocar being extended through the abdominal wall.

FIG. 39 shows a secondary balloon 138 positioned to shield the balloon 130 from puncture by a trocar 140. While this secondary balloon is optional, its benefit is apparent where it become necessary to pierce the abdominal wall after placement of the balloon 130.

Figure 40:
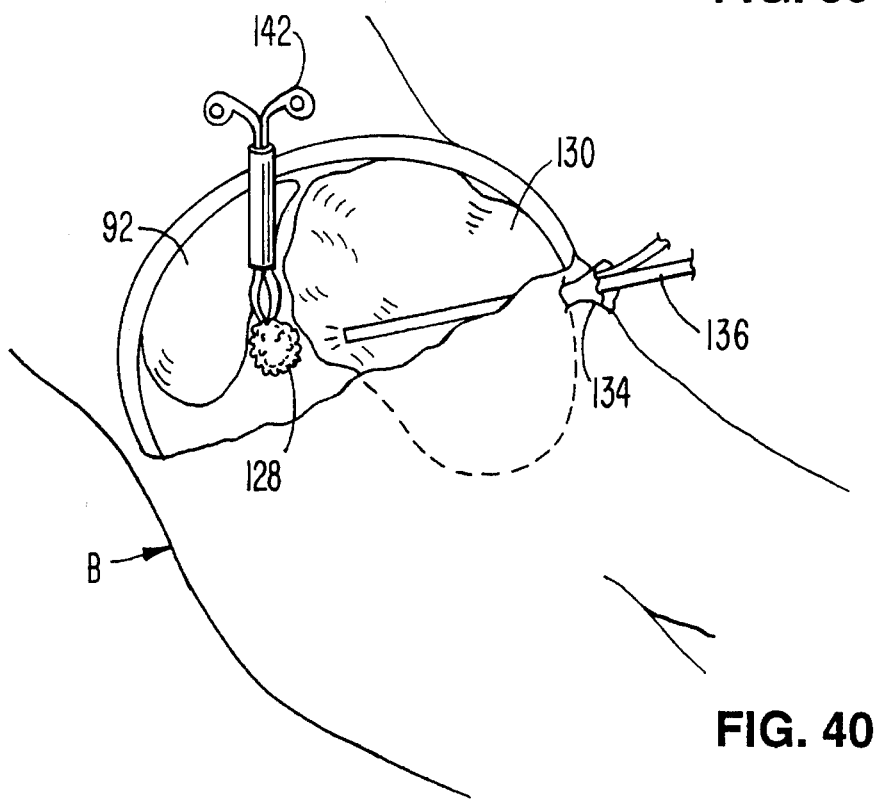
FIG. 40 is a perspective view of the lifting device of the fifteenth embodiment shown in place within the abdominal cavity of a body, with parts broken away for illustration and laparoscopic forceps extended into gripping engagement with the gallbladder.
Figure 41:
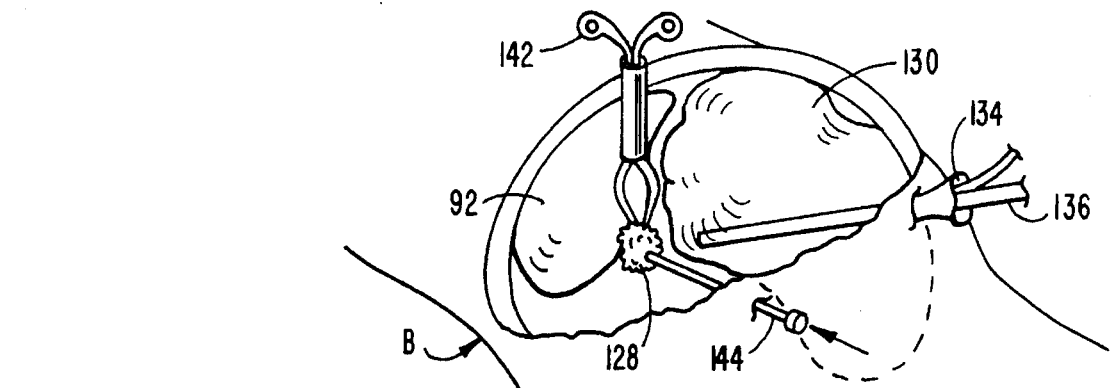
FIGS. 41, 42 and 43 are perspective views of the lifting device of the fifteenth embodiment of the invention in place within the abdominal cavity of a body, sequentially illustrating the steps of inserting the gallbladder distension and manipulation device of the invention laparoscopically into the abdominal cavity and into gripping engagement with the gallbladder.
Figure 42:
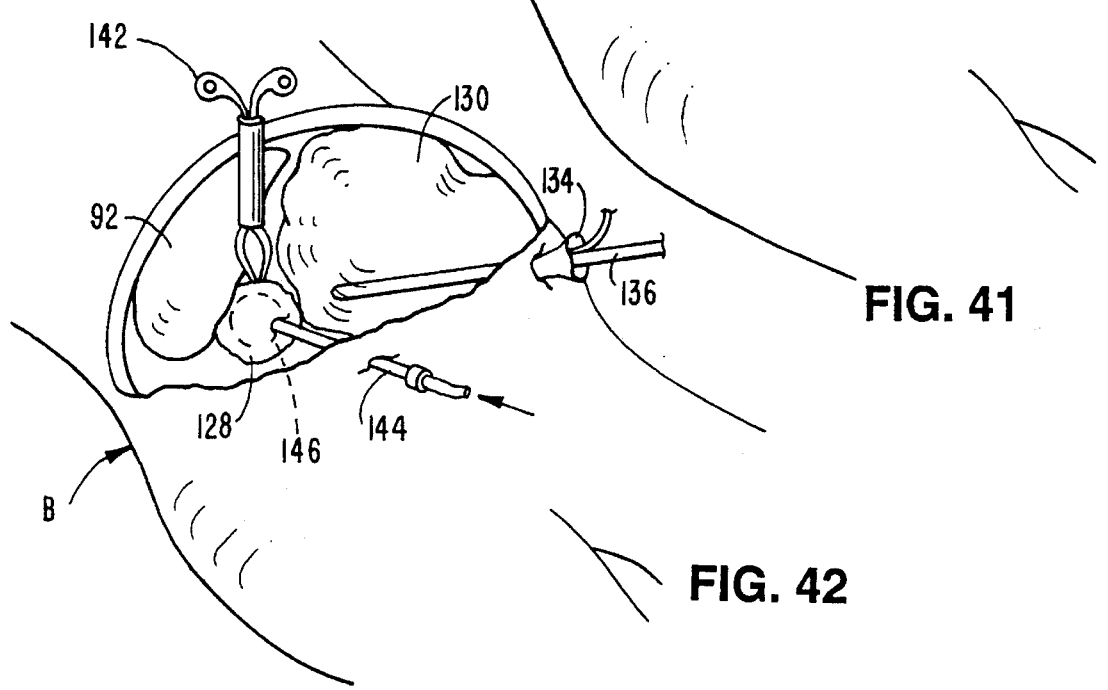
Figure 43:
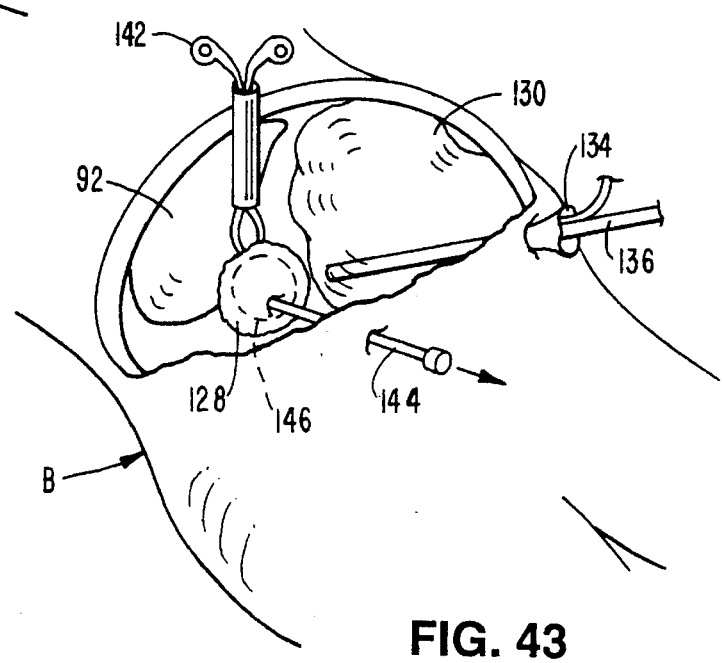

FIG. 40 shows forceps 142 laparoscopically extended into gripping engagement with the gallbladder 128. With the gallbladder so gripped, a laparoscopic distension, manipulation and removal tool 144 is extended into the abdominal cavity in piercing engagement with the gallbladder. The tool takes the form of a dual lumen tubular needle having a sharpened open end 147 through which the contents of the gallbladder may be drawn and an annular balloon 146 which may be inflated through a lumen of the tool communicating therewith (see FIG. 45).

Once the tool has evacuated the contents of the gallbladder, the balloon 146 is inflated and assumes internal gripping engagement with the gallbladder. The tool may then be manipulated, thus maneuvering the gallbladder within the abdominal cavity or pulling it out of the abdominal cavity, as depicted by the arrow line in FIG. 43. Depending upon the size of the gallbladder, the removal of the organ may require some enlargement of the incision through which the tool extends. The forceps would be released from the gallbladder to permit its distension, manipulation or withdrawal from the abdominal cavity. The entire procedure is viewed through the endoscope 136.

The device of FIG. 45 corresponds to that of FIG. 44, except that the tubular needle of the tool $144_a$ has a single lumen only for inflation of the balloon $146_a$ and that the needle does not extend fully through the balloon. Thus, the FIG. 45 embodiment cannot be used to evacuate the gallbladder.

Figure 38:
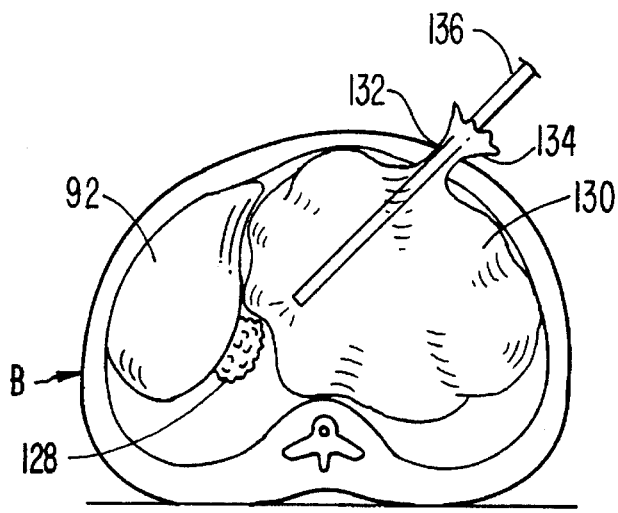
FIG. 38 is a transverse cross-sectional elevational view of a body showing a fifteenth embodiment of the invention in the process of lifting the abdominal wall and displacing the liver for exposure of the gallbladder, with an endoscope shown in place within the lifting device.

The embodiment of FIG. 46 corresponds to that of FIG. 38, except that a tube 148 is sealed to and extends fully through the balloon $130_a$ to accommodate extension of the endoscope 136 fully through the balloon. With the FIG. 46 embodiment, the gallbladder 128 is viewed directly, rather than through the balloon.

CONCLUSION

From the foregoing description, it is believed apparent that the present invention provides an improved technique for retracting the abdominal wall without insufflation. It also provides improved operating techniques. It should be understood, however, that the invention is not intended to be limited to the specifics of the illustrated embodiments, but rather is defined by the accompanying claims.

We claim:

1. A method of lifting the abdominal wall for peritoneal retraction during laparoscopic surgery, said method comprising:

(a) forming a small laparoscopic opening of limited area in the abdominal wall;

(b) inserting a balloon through the opening in a contracted state to dispose said balloon beneath abdominal wall, said balloon comprising a primary balloon element having an open central portion with a secondary balloon element therein inflatable to laterally extend the primary balloon element;

(c) expanding the lifting device from the exterior of the abdominal wall by inflating the secondary balloon element to expand the device interiorly of the abdominal wall laterally beyond the limited area of the laparoscopic opening and interiorly engage an extensive area of the abdominal wall; and, (d) lifting the abdominal wall with the device by inflating the primary balloon element.

2. Apparatus for lifting the abdominal wall for peritoneal retraction, said apparatus comprising:

(a) a balloon insertable through a small laparoscopic incision of limited area in the abdominal wall, said balloon being expansible from the exterior of the abdominal wall laterally beyond the limited area of the laparoscopic incision to interiorly engage an extensive area of the abdominal wall, being fabricated of a generally inelastic flexible material shaped to expand into engagement with an extended area of the abdominal wall upon inflation, and comprising a plurality of stacked toroidal chambers; and, (b) means to selectively inflate the chambers to impart lifting force to the abdominal wall through the balloon.

3. Apparatus according to claim 2 further comprising a membrane secured to the balloon to extend across the toroidal chambers when the balloon is inflated.

4. Apparatus according to claim 3 wherein the membrane is apertured to provide access therethrough.

5. Apparatus for lifting the abdominal wall for peritoneal retraction, said apparatus comprising:

(a) a primary balloon insertable through a small laparoscopic incision of limited area in the abdominal wall, said primary balloon being expansible from the exterior of the abdominal wall laterally beyond the limited area of the laparoscopic incision to interiorly engage an extensive area of the abdominal wall, being fabricated of a generally inelastic flexible material and being toroidal and shaped to expand into engagement with an extended area of the abdominal wall upon inflation;

(b) a secondary balloon within the primary balloon, said secondary balloon being inflatable to laterally expand the primary balloon; and (c) means to selectively inflate the primary balloon to impart lifting force to the abdominal wall through the primary balloon.

6. Apparatus for lifting the abdominal wall for peritoneal retraction, said apparatus comprising:

(a) a balloon insertable through a small laparoscopic incision of limited area in the abdominal wall, said balloon being expansible from the exterior of the abdominal wall laterally beyond the limited area of the laparoscopic incision to interiorly engage an extensive area of the abdominal wall, and being fabricated of a generally inelastic flexible material shaped to expand laterally into engagement with an extended area of the abdominal wall upon inflation; and (b) means to selectively expand the balloon against the abdominal wall to impart lifting force to the abdominal wall through the balloon.

7. Apparatus for lifting the abdominal wall for peritoneal retraction, said apparatus comprising:

(a) a balloon insertable through a small laparoscopic incision of limited area in the abdominal wall, said balloon being expansible from the exterior of the abdominal wall laterally beyond the limited area of the laparoscopic incision to interiorly engage an extensive area of the abdominal wall, being fabricated of a generally inelastic flexible material and being toroidal and shaped to expand into engagement with an extended area of the abdominal wall upon inflation;

(b) a membrane extending across the balloon to drape body tissue when the balloon is expanded beneath the abdominal wall; and (c) lifting means to selectively force the balloon against the abdominal wall to impart lifting force thereto.

* * * * *